United States Patent [19]
Thundat

[11] Patent Number: 5,918,263
[45] Date of Patent: Jun. 29, 1999

[54] MICROCANTILEVER DETECTOR FOR EXPLOSIVES

[75] Inventor: Thomas G. Thundat, Knoxville, Tenn.

[73] Assignee: Lockheed Martin Energy Research Corporation, Oak Ridge, Tenn.

[21] Appl. No.: 09/052,252

[22] Filed: Mar. 31, 1998

[51] Int. Cl.⁶ .......................... G01N 25/20; G01N 30/96; H02N 10/00
[52] U.S. Cl. ...................... 73/35.16; 73/35.14; 73/31.02; 73/31.05; 422/88; 310/306
[58] Field of Search .................. 422/88, 91, 94, 422/95; 310/306, 307; 73/25.01, 28.05, 35.15, 35.16, 35.14, 23.2, 31.02, 31.03, 31.05

[56] References Cited

U.S. PATENT DOCUMENTS

| 5,445,008 | 8/1995 | Wachter | 73/24.06 |
| 5,719,324 | 2/1998 | Thundat | 73/24.01 |

OTHER PUBLICATIONS

Kirk–Othmer Encyclopedia of Chemical Technology, Third Edition vol. 9, "Explosives and Propellants," pp. 561–605.
Journal of Energetic Materials, 1992, 814, "TNT Vapour Measurements Above Buried Landmines", pp. 292–307.

*Primary Examiner*—Michael Brock
*Assistant Examiner*—Jay L. Politzer
*Attorney, Agent, or Firm*—J. Kenneth Davis

[57] ABSTRACT

Methods and apparatus for detecting the presence of explosives by analyzing a vapor sample from the suspect vicinity utilize at least one microcantilever. Explosive gas molecules which have been adsorbed onto the microcantilever are subsequently heated to cause combustion. Heat, along with momentum transfer from combustion, causes bending and a transient resonance response of the microcantilever which may be detected by a laser diode which is focused on the microcantilever and a photodetector which detects deflection of the reflected laser beam caused by heat-induced deflection and resonance response of the microcantilever.

32 Claims, 1 Drawing Sheet

MICROCANTILEVER DETECTOR FOR EXPLOSIVES

CROSS-REFERENCE TO RELATED APPLICATIONS

The invention hereinafter described and claimed relates to the following, which are herein incorporated in their entirety by reference: U.S. Pat. No. 5,445,008 Microbar Sensor, by Eric A. Wachter and Thomas G. Thundat, filed Mar. 24, 1994 and issued Aug. 29, 1995; and U.S. Pat. No. 5,719,324 Microcantilever Sensor, by Thomas G. Thundat and Eric A. Wachter, filed Jun. 16, 1995 and issued Feb. 17, 1998.

The United States Government has rights in this invention pursuant to contract no. DE-AC05-96OR22464 between the United States Department of Energy and Lockheed Martin Energy Research Corporation.

FIELD OF THE INVENTION

The present invention relates to methods and apparatus for detecting explosive vapors, and especially for detecting the presence of land mines, unexploded ordinance, hidden explosives, and the like, and more particularly to methods and apparatus for detecting explosive vapors using detection apparatus comprising very small cantilever elements, hereinafter called cantilevered springs, cantilevers, or microcantilevers.

BACKGROUND OF THE INVENTION

There is an increasing demand to perform real-time detection of hidden explosive devices such as explosives concealed in luggage, land mines, unexploded ordinance, and the like. This is an ever-growing problem due to the extreme low cost of explosive devices and the ease with which they can be deployed. For one example, security concerns at sensitive locations such as airports require that baggage and freight as well as personal effects be carefully screened for explosive devices. Such devices may be small and innocuous, and may not be readily detectable by other more conventional means such as visual inspection, x-ray or magnetic detection techniques. For a second example, antipersonnel land mines are relatively small devices generally constructed from plastic and other non-metallic materials. more than 110 million active mines are scattered in 64 countries. Also more mines are in stockpiles in countries all over the world. Many countries are infested with land mines. At the current rate, for every mine removed 20 more are laid. Every month over 2,000 people are killed or maimed by mine explosions. Old mine fields remain active, endangering non-combatants long after the war where they were used is over. On average, locating a single land mine is 100 times more expensive than the cost of the mine. It is estimated that at the current rate of removal, it will take a few thousand years to remove the land mines that already infest many countries. In addition to the humanitarian need for eliminating old mines, methods and apparatus for readily detecting and de-fusing land mines are needed by the Department of Defense.

Because many land mines are made of non-metallic substances, it is desirable to locate them using chemical techniques. Since the vapor pressures of many explosive substances are very low, a chemical detection technique with sensitivity of parts per trillion to parts per quadrillion is needed. Such high sensitivity now is achievable only with techniques such as mass spectroscopy or nuclear magnetic resonance, which require large and complex equipment. None of the technology currently available offers an extremely sensitive, hand-held, battery-operated explosive detector. An explosive detector that can give no false reading and can pinpoint explosive devices such as explosives concealed in luggage, unexploded ordinance and land mines with high efficiency is much needed in both military and civilian applications.

OBJECTS OF THE INVENTION

Accordingly, it is an object of the present invention to provide new and improved methods and apparatus for detecting explosive vapors, such as are present in extremely low concentrations in the vicinity of hidden explosives, buried land mines, unexploded ordinance, and the like; as well as for detecting explosive gases such as hydrogen, methane, propane, and the like in much higher concentrations for more conventional safety applications.

It is another object to provide a new and improved method and apparatus for detecting explosive vapors using detection apparatus comprising microcantilevers.

Further and other objects of the present invention will become apparent from the description contained herein.

SUMMARY OF THE INVENTION

In accordance with one aspect of the present invention, the foregoing and other objects are achieved by an apparatus for detecting the presence of an explosive vapor phase chemical in a monitored atmosphere, which comprises: at least one cantilevered spring element having at least one region treated with at least one adsorbent having an adsorptive affinity for the explosive vapor phase chemical; heater means for increasing the surface temperature of at least a portion of the cantilevered spring element to a temperature sufficient to cause combustion of the adsorbed explosive vapor phase chemical thereby causing deflection of the cantilevered spring element; and deflection detection means for detecting deflection of the cantilevered spring element due to combustion of the adsorbed vapor phase chemical. In accordance with a second aspect of the present invention, the foregoing and other objects are achieved by A method for detecting the presence of an explosive vapor phase chemical in a monitored atmosphere which comprises the steps of: providing a cantilevered spring element having at least one region treated with at least one adsorbent having an adsorptive affinity for the explosive vapor phase chemical to adsorb the explosive vapor phase chemical; Providing a heater means for increasing the surface temperature of at least a portion of the cantilevered spring element to a temperature sufficient to cause combustion of the adsorbed explosive vapor phase chemical; exposing the cantilevered spring element in the monitored atmosphere; operating the heating means to increase the surface temperature of the at least one heated portion of the cantilevered spring element to a temperature sufficient to cause combustion of the adsorbed explosive vapor phase chemical thereby causing deflection of the cantilevered spring element; and detecting deflection of the cantilevered spring element due to combustion of adsorbed vapor phase chemical to determine the presence of adsorbed explosive vapor phase chemical.

Figure 1:
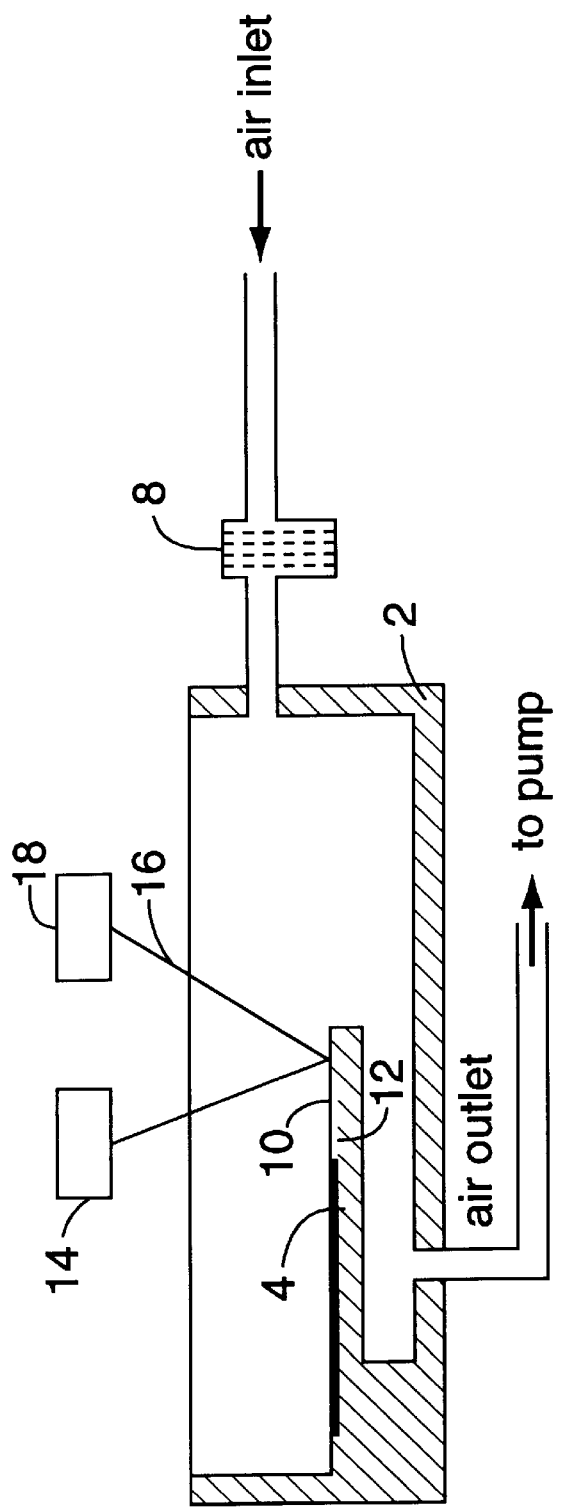
FIG. 1 shows one embodiment with a detection system using a diode laser and position sensitive detector.
Figure 2:
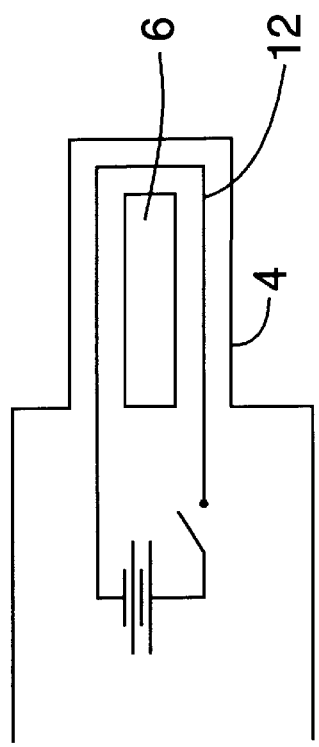
FIG. 2 shows an embodiment with an imbedded piezoresistive track and its electric current supply.

For a better understanding of the present invention, together with other and further objects, advantages and capabilities thereof, reference is made to the following disclosure and appended claims in connection with the above-described drawing.

DETAILED DESCRIPTION OF THE INVENTION

The present invention is based on the fact that explosive devices such as hidden explosives, buried land mines, and other unexploded ordinance leak out an extremely small concentration of vapors from the explosives. For example, the estimated concentration of these vapors is around sub-ppt above the soil where a land mine is buried. Detection of such small quantities of vapors requires very sophisticated techniques. however, the present invention describes a novel and extremely sensitive technique for detecting vapors from hidden explosives, land mines and unexploded ordinances with a sensitivity of parts per quadrillion.

The microcantilever of the present invention preferably comprises a silicon microcantilever that is located and enclosed within a small chamber. Typical dimensions of these microcantilevers are 1–200 $\mu$m long, 1–40 $\mu$m wide and 0.1–3 $\mu$m thick. The mass of a microcantilever can vary from a small fraction of a nanogram to a few nanograms. Coating one side of these microcantilevers with a material having a different coefficient of thermal expansion, such as a metal film, makes them extremely sensitive to temperature variations as they bend due to differential thermal expansion. In one embodiment, the bending of the microcantilever can be detected by an optical method. As the temperature of the microcantilever changes, the microcantilever's deflection changes due to differential thermal expansion, sometimes called bimetallic effect, and can be detected with sub nanometer resolution. A temperature variation of $10^{-6}$° K. can be easily detected by the microcantilever method. The estimated minimum detectable power level using an unoptimized microcantilever is on the order of a pW, corresponding to a detectable energy of femto joule. Using an optimally designed microcantilever, the sensitivity can be improved even further.

In one embodiment of this invention air from the vicinity of a suspected explosive such as a buried land mine is drawn into chamber 2 containing the microcantilever 4 with coating 6. Coating 6 may comprise platinum or transition metal oxides and other elements, compounds, and compositions well-known to the skilled artisan as adsorbers of explosive vapor molecules. Dust and other particulate are removed by filter 8 to avoid interferences. As the sampling continues the molecules of explosive vapors adsorb and accumulate on microcantilever surface 10. At the end of sampling the microcantilever is heated gradually to a high temperature by piezoresistive track 12 implanted in the microcantilever or by passing current through the microcantilever itself if it is conductive or semiconductive, for example doped silicon. Since the thermal mass of the microcantilever is extremely small, a microcantilever can be heated to a few hundred degrees centigrade and cooled to an ambient temperature in a short time, which may be a fraction of a second to a few seconds. The microcantilever is heated and held at temperature for a predetermined amount of time. The microcantilever undergoes drastic bending as the microcantilever is heated. Once the steady state is reached the microcantilever bending stabilizes except for the random noise in the power supply. Once the auto combustion temperature is maintained for a characteristic period of time the adsorbed molecules of explosives undergo auto-combustion producing a sudden variation in the microcantilever deflection. The auto combustion temperature and the time the temperature needs to be maintained for the combustion to occur are characteristics of individual explosives. The sudden deflection is due to both momentum and heat transfer due to combustion of the explosive molecules. First, combustion of explosive molecules produces a transient in the cantilever response. This mechanical impulse is detected by the bending detection means and is interpreted to indicate combustion of explosive molecules. Second, in the embodiment comprising preferrably a metal coating on a region of the cantilevered spring, combustion of explosive molecules also produces additional heat input into the cantilevered spring, which in turn causes additional deflection of the cantilevered spring due to differential expansion of the cantilevered spring and its coating. In this manner, the effect of the combustion of explosive molecules on the cantilevered spring is amplified. This sudden deflection produces a resonance transient where the deflection amplitude falls off exponentially as the function of time and Q-factor of the microcantilever. The frequency of the transient is the same as the microcantilever resonance frequency. The characteristic transient due to combustion will be superimposed on the random fluctuation of the microcantilever due to unsteadiness or noise in the power supply. The characteristic transient can be separated from the random fluctuations using wavelet signal processing.

The exact temperature of the microcantilever can be measured from the variation in the microcantilever resistance. Therefore, a plot of normalized microcantilever bending, with respect to a reference microcantilever, will show characteristic transient if explosive molecules are present. The transients will be a signal to alert the operator of the device to the presence of the explosive vapor. Using this approach to detection sensitivity in the sub ppt-ppq level is calculated for a sampling time of 1 second.

In one embodiment, the transient resonance response is detected by a photodetector 14 which detects a laser light beam 16 emitted from a laser diode 18 and reflected by the microcantilever surface. A plot of normalized microcantilever bending, with respect to a reference microcantilever, will indicate if explosive molecules are present.

Simple calculations show that a sensitivity of parts per quadrillion (ppq) can be easily achieved using this technique for molecules of energetic materials such as TNT. An adsorption concentration as low as one per 10,000 sites on the microcantilever is enough for producing detectable bending of the microcantilever.

Following is an example estimate of sensitivity: Assuming a TNT vapor concentration of 0.1 ppb above a hidden explosive, we can show that the proposed device has a theoretical sensitivity to detect TNT molecules with sub-ppt for one second sampling time. Using a commercially available small pump, 12.5 cc of air can be drawn into the chamber in one second. The number of TNT molecules in this volume is about $3.3 \times 10^{10}$. A conservative equilibrium constant of distribution of TNT molecules in air and on the microcantilever surface, 0.01, is assumed (sticking coefficient 0.01). This gives a surface concentration of $3.3 \times 10^7$ molecules of TNT per square centimeter. Taking into account of the surface area of the chamber, differential sticking coefficient of the microcantilever surface and chamber, and time, a reasonable estimate of the number of molecules on the microcantilever surface can be derived. Since the exposed area of a microcantilever is $10^{-4}$ cm$^2$, the weight of TNT molecules adsorbed on the microcantilever is $1.25 \times 10^{-16}$ g. The heat of combustion of TNT is 15.06 kJ/g and the ignition temperature is 310 degrees centigrade. The microcantilever may be heated to 310° C. in a fraction of a second causing the submonolayer of TNT to undergo combustion. Therefore, the total amount of heat generated is about 1.85E-13J. The time for such explosion is estimated to be microseconds. Using a conservative figure of 10 $\mu$s and an impulse equation, a transient amplitude of 2.2 nm can be calculated for a microcantilever with a nano gram mass and with a spring constant in the range of $10^{-3}$N/m. Therefore, an optimized device will be able to detect explosion due to submonolayers of adsorbed TNT on a microcantilever. The overall sensitivity of the device, however, can be improved by at least three orders of magnitude by following optimization techniques. It has been demonstrated that the amount of TNT molecules adsorbed on a surface can be improved by an order of magnitude by coating the surface with adsorbent materials. The surface area of the microcantilever can be increased by a factor of ten by microcantilever design and by increasing the surface roughness. Detection of the microcantilever bending can also be optimized for improved sensitivity. Therefore, the proposed device, once optimized, is capable of detecting TNT vapors with parts per quadrillion sensitivity. At this high sensitivity the device can detect hidden explosives such as explosive devices concealed in luggage, buried land mines, and unexploded ordinance.

The claimed invention also exhibits a high degree of selectivity. Because of its extremely high sensitivity, the microcantilever detector for explosives can also be used in detecting other explosives with even lower vapor pressure, such as RDX. The detector can also distinguish other explosives, since the combustion temperature is different for different explosives (TNT=310C, RDX=260C, etc. for 5 seconds. The time can be reduced to 0.1 second by increasing the temperature, for example, 575C for TNT is 0.1 second). The only interference can come from other explosive gases such as gasoline, etc. This, however, can be identified and accounted for because each explosive vapor has a characteristic temperature of combustion. In addition, energetic molecules have combustion energy about two orders of magnitude higher than regular molecules. Selectivity may be achieved by using multiple different microcantilevers, each operating at characteristic temperatures of different explosives. Since microcantilevers are inherently compatible with array design, an array design can detect many different explosives. Since the microcantilevers are extremely small, a continuously operating device may be built to avoid any lost time by having an array of microcantilevers sampling at different rates. The microcantilever sensitivity can be improved by optimization techniques and by using catalysts (for example, transition metal oxides) for increased adsorption of explosive molecules on the microcantilever surface.

One of the interferants in the operation of a microcantilever detector is the presence of other explosive gases such as gasoline, hydrogen, and the like. Most of these explosive gas molecules adsorbed on the microcantilever surface will burn off when the temperature of the microcantilever is raised rapidly to a steady state. However, when concentration of explosive gas vapors are very high a modified microcantilever can be used to detect the explosive gases. In this application, the microcantilever is coated with a catalytic metal. As the temperature of the microcantilever is raised, the explosive gases, if present in the ambient at concentration near the explosive limit (around a few percent) will undergo explosion. This will cause a sudden change in temperature of the microcantilever. This temperature change can be detected either by deflection of the microcantilever or by change in the resistance of a metal film or filament such as platinum on the microcantilever.

In various embodiments, microcantilever movement or deflection can be detected by a variety of means well-known to the skilled artisan, including optical techniques, piezoresistance, or capacitance variation.

In another embodiment, explosive gases may be detected wherein the gas in the vicinity of the microcantilever is exploded by a hot microcantilever coated with a catalyst such as platinum. In such an embodiment, the variation in resistance of a metal coating such as platinum on the microcantilever may be used as a detection means.

The temperature required to explode or combust the explosive, either adsorbed on the microcantilever or ambient to the microcantilever, can be lowered by using catalysts on the microcantilever.

Since the microcantilevers are extremely small, a continuously operating device may be built which avoids any dead time. There may also be different microcantilevers sampling at different rates providing a high sensitivity of detection. The microcantilever sensitivity can be improved by optimization techniques and by using catalysts for increased adsorption on the microcantilever surface.

Unique features and advantages of the methods and apparatus described herein include: Both the apparatus and the methods of using the apparatus to detect the presence of explosive vapors are inherently simple. The apparatus is extremely sensitive and easily miniaturized. The apparatus is compact and light weight. The microcantilevers can be micromachined. Additional microcantilevers can be used for flow rate and pressure. The present invention can be easily incorporated into other microcantilever sensor concepts in an array design. The apparatus of the present invention can use battery power for the electronic components. The apparatus is capable of regenerating itself for reuse after each cycle. The apparatus is rugged, robust, and is easily transportable.

While there has been shown and described what are at present considered the preferred embodiments of the invention, it will be obvious to those skilled in the art that various changes and modifications can be made therein without departing from the scope of the inventions defined by the appended claims.

What is claimed is:

1. An apparatus for detecting the presence of an explosive vapor phase chemical in a monitored atmosphere, comprising:

A at least one cantilevered spring element having at least one region treated with at least one adsorbent having an adsorptive affinity for the explosive vapor phase chemical, B heater means for increasing the surface temperature of at least a portion of the cantilevered spring element to a temperature sufficient to cause combustion of the adsorbed explosive vapor phase chemical thereby causing deflection of the cantilevered spring element; and C deflection detection means for detecting deflection of the cantilevered spring element due to combustion of the adsorbed vapor phase chemical.

2. The apparatus for detecting the presence of an explosive vapor phase chemical in a monitored atmosphere as described in claim 1, the cantilevered spring element further comprising a catalyst layer bonded on at least one catalyzed region of the cantilevered spring element.

3. The apparatus for detecting the presence of an explosive vapor phase chemical in a monitored atmosphere as described in claim 1, wherein the cantilevered spring element comprises a first material having a first coefficient of thermal expansion and a coating bonded on at least one coated region, the coating comprising a second material having a second coefficient of thermal expansion, the first coefficient of thermal expansion and the second coefficient of thermal expansion being unequal.

4. The apparatus for detecting the presence of an explosive vapor phase chemical in a monitored atmosphere as described in claim 1 wherein the cantilevered spring element comprises a semiconducting material.

5. The apparatus for detecting the presence of an explosive vapor phase chemical in a monitored atmosphere as described in claim 1 wherein the heater means comprises a piezoresistive track implanted in the at least one portion of the cantilevered spring element and means for supplying an electric current therethrough.

6. The apparatus for detecting the presence of an explosive vapor phase chemical in a monitored atmosphere as described in claim 1 wherein the heater means comprises a suitably configured conductive path comprising the at least one portion of the cantilevered spring element and means for supplying an electric current therethrough.

7. The apparatus for detecting the presence of an explosive vapor phase chemical in a monitored atmosphere as described in claim 1 wherein the deflection detection means comprises a laser emitting means for emitting a laser light beam and a laser detecting means for detecting the laser light beam, the laser emitting means being disposed to emit the laser beam against the cantilevered spring element.

8. The apparatus for detecting the presence of an explosive vapor phase chemical in a monitored atmosphere as described in claim 2 wherein the deflection detection means comprises a means for detecting at least one change in at least one electrical characteristic of the catalyst layer.

9. The apparatus for detecting the presence of an explosive vapor phase chemical in a monitored atmosphere as described in claim 3 wherein the second material comprises a metal.

10. An apparatus for detecting the presence of an explosive vapor phase chemical in a monitored atmosphere as described in claim 4 wherein the semiconducting material comprises silicon.

11. The apparatus for detecting the presence of an explosive vapor phase chemical in a monitored atmosphere as described in claim 5 wherein the deflection detection means comprises a means for detecting at least one change in at least one electrical characteristic of the piezoresistive track.

12. The apparatus for detecting the presence of an explosive vapor phase chemical in a monitored atmosphere as described in claim 6 wherein the deflection detection means comprises a means for detecting at-least one change in at least one electrical characteristic of the at least one portion of the cantilevered spring element.

13. The apparatus for detecting the presence of an explosive vapor phase chemical in a monitored atmosphere as described in claim 7 wherein the laser detecting means is disposed for detecting a reflection of the laser light beam from the spring element and emitting an output signal corresponding to the deflection of the cantilevered spring element.

14. The apparatus for detecting the presence of an explosive vapor phase chemical in a monitored atmosphere as described in claim 7 wherein the laser emitting means comprises a laser diode.

15. The apparatus for detecting the presence of an explosive vapor phase chemical in a monitored atmosphere as described in claim 7 wherein the laser detecting means comprises a photodetector.

16. The apparatus for detecting the presence of an explosive vapor phase chemical in a monitored atmosphere as described in claim 7 wherein the bending detection means further comprises an amplification circuit suitably configured and disposed for amplifying the output signal of the laser detecting means.

17. A method for detecting the presence of an explosive vapor phase chemical in a monitored atmosphere comprising the steps of:

A providing a cantilevered spring element having at least one region treated with at least one adsorbent having an adsorptive affinity for the explosive vapor phase chemical to adsorb the explosive vapor phase chemical;

B Providing a heater means for increasing the surface temperature of at least a portion of the cantilevered spring element to a temperature sufficient to cause combustion of the adsorbed explosive vapor phase chemical;

C exposing the cantilevered spring element in the monitored atmosphere;

D operating the heating means to increase the surface temperature of the at least one heated portion of the cantilevered spring element to a temperature sufficient to cause combustion of the adsorbed explosive vapor phase chemical thereby causing deflection of the cantilevered spring element; and E detecting deflection of the cantilevered spring element due to combustion of adsorbed vapor phase chemical to determine the presence of adsorbed explosive vapor phase chemical.

18. The method for detecting the presence of an explosive vapor phase chemical in a monitored atmosphere as described in claim 17 wherein the step of providing a cantilevered spring element is accomplished by providing a cantilevered spring element further comprising a catalyst layer bonded on at least one catalyzed region of the cantilevered spring element.

19. The method for detecting the presence of an explosive vapor phase chemical in a monitored atmosphere as described in claim 17 wherein in the step of providing a cantilevered spring element is accomplished by providing a cantilevered spring element comprising a first material having a first coefficient of thermal expansion and a coating bonded on at least one coated region, the coating comprising a second material having a second coefficient of thermal expansion, the first coefficient of thermal expansion and the second coefficient of thermal expansion being unequal.

20. The method for detecting the presence of an explosive vapor phase chemical in a monitored atmosphere as described in claim 17 wherein the step of providing a cantilevered spring element is accomplished by providing a cantilevered spring element comprising a semiconducting material.

21. The method for detecting the presence of an explosive vapor phase chemical in a monitored atmosphere as described in claim 17 wherein the step of providing a heater means is accomplished by providing piezoresistive track implanted in the at least one portion of the cantilevered spring element and means for supplying an electric current thereto.

22. The method for detecting the presence of an explosive vapor phase chemical in a monitored atmosphere as described in claim 17 wherein the step of providing a heater means is accomplished by configuring the at least one heated portion of the cantilevered spring element for conducting an electric current therethrough and providing means for supplying an electric current thereto.

23. The method for detecting the presence of an explosive vapor phase chemical in a monitored atmosphere as described in claim 17 wherein the step of providing a deflection detection means is accomplished by the steps of providing a laser emitting means for emitting a laser light beam and providing a laser detecting means for detecting the laser light beam, the laser emitting means being disposed to emit the laser beam against the cantilevered spring element.

24. The method for detecting the presence of an explosive vapor phase chemical in a monitored atmosphere as described in claim 18 wherein the step of detecting deflection of the cantilevered spring element is accomplished by detecting at least one change in at least one electrical characteristic of the catalyst layer on the cantilevered spring element.

25. The method for detecting the presence of an explosive vapor phase chemical in a monitored atmosphere as described in claim 19 wherein the step of providing a cantilevered spring element is accomplished by further providing the cantilevered spring element with a metal coating bonded on the at least one coated region.

26. The method for detecting the presence of an explosive vapor phase chemical in a monitored atmosphere as described in claim 20 wherein the step of providing the cantilevered spring element is accomplished by providing a cantilevered spring element comprising silicon.

27. The method for detecting the presence of an explosive vapor phase chemical in a monitored atmosphere as described in claim 21 wherein the step of providing the deflection detection means is accomplished by providing means for detecting a change in an electrical characteristic of the piezoresistive track.

28. The method for detecting the presence of an explosive vapor phase chemical in a monitored atmosphere as described in claim 22 wherein the step of providing a deflection means is accomplished by providing means for detecting a change in an electrical characteristic of the at least one heated portion of the cantilevered spring element.

29. The method for detecting the presence of an explosive vapor phase chemical in a monitored atmosphere as described in claim 23 wherein the step of providing the laser detecting means is further accomplished by disposing the laser detecting means for detecting a reflection of the laser light beam from the spring element and configuring the laser detecting means to emit an output signal corresponding to the deflection of the cantilevered spring element.

30. The method for detecting the presence of an explosive vapor phase chemical in a monitored atmosphere as described in claim 23 wherein the step of providing a laser emitting means is accomplished by providing a laser diode.

31. The method for detecting the presence of an explosive vapor phase chemical in a monitored atmosphere as described in claim 23 wherein the step of providing a laser detecting means is accomplished by providing a photodetector.

32. The method for detecting the presence of an explosive vapor phase chemical in a monitored atmosphere as described in claim 23 wherein the step of providing a bending detecting means is further accomplished by the additional step of providing an amplification circuit suitably configured and disposed for amplifying the output signal of the laser detecting means.

\* \* \* \* \*